United States Patent
Deng et al.

(10) Patent No.: US 10,664,567 B2
(45) Date of Patent: May 26, 2020

(54) EXTRACTION OF INFORMATION FROM AN IMAGE AND INCLUSION THEREOF IN A CLINICAL REPORT

(71) Applicant: KONINKLIJKE PHILIPS N.V., Eindhoven (NL)

(72) Inventors: Yinhui Deng, Shanghai (CN); Qi Zhong Lin, Shanghai (CN); Lilla Boroczky, Mount Kisco, NY (US); Michael Chun-Chieh Lee, Lexington, MA (US); Ying Wu, Shanghai (CN)

(73) Assignee: Koninklijke Philips N.V., Eindhoven (NL)

(*) Notice: Subject to any disclaimer, the term of this patent is extended or adjusted under 35 U.S.C. 154(b) by 43 days.

(21) Appl. No.: 15/109,700

(22) PCT Filed: Jan. 12, 2015

(86) PCT No.: PCT/IB2015/050214
§ 371 (c)(1),
(2) Date: Jul. 5, 2016

(87) PCT Pub. No.: WO2015/110932
PCT Pub. Date: Jul. 30, 2015

(65) Prior Publication Data
US 2016/0328517 A1    Nov. 10, 2016

Related U.S. Application Data

(60) Provisional application No. 61/931,735, filed on Jan. 27, 2014.

(51) Int. Cl.
*G06F 17/24*    (2006.01)
*G06K 9/00*    (2006.01)
(Continued)

(52) U.S. Cl.
CPC .......... *G06F 19/321* (2013.01); *G06F 17/241* (2013.01); *G06K 9/00449* (2013.01);
(Continued)

(58) Field of Classification Search
None
See application file for complete search history.

(56) References Cited

U.S. PATENT DOCUMENTS 5,807,256 A * 9/1998 Taguchi ............... G06F 19/321
                                                   600/300
7,242,806 B2   7/2007 Johnson et al.
(Continued)

OTHER PUBLICATIONS

You et al., "Figure content analysis for improved biomedical article retrieval," Electronic Imaging, SPIE vol. 7247, 72470V, 2009.*
(Continued)

*Primary Examiner* — Soo Shin

(57) ABSTRACT

A method includes obtaining, in electronic format, an image (102) including a medical image display region (104) and an information display region (106). The at least one of the medical image display region or the information display region includes graphical indicia representing at least one of an annotation (110, 112, 114, 116) or alphanumeric information (118, 120, 122, 124, 126, 128, 130, 132, 134, 136, 138, 140). The method further includes evaluating pixels of the image to identify pixels including the graphical indicia representing an annotation or alphanumeric information of interest in the image. The method further includes extracting the annotation or alphanumeric information of interest from the identified graphical indicia from the image. The method further includes inserting the extracted annotation or alphanumeric information of interest in an electronically formatted clinical report for the image.

11 Claims, 4 Drawing Sheets

(51) Int. Cl.
*G06K 9/20* (2006.01)
*G06K 9/32* (2006.01)
*G06K 9/46* (2006.01)
*G16H 15/00* (2018.01)
*G06F 19/00* (2018.01)

(52) U.S. Cl.
CPC ....... *G06K 9/00456* (2013.01); *G06K 9/2063* (2013.01); *G06K 9/3266* (2013.01); *G06K 9/4604* (2013.01); *G16H 15/00* (2018.01); *G06K 2209/01* (2013.01)

(56) References Cited

U.S. PATENT DOCUMENTS

| | | | | |
|---|---|---|---|---|
| 8,533,204 | B2* | 9/2013 | Serrano | G06K 9/3258 |
| | | | | 707/749 |
| 9,129,044 | B2 | 9/2015 | Shin et al. | |
| 9,280,709 | B2* | 3/2016 | Suzuki | G06F 16/739 |
| 2007/0019853 | A1 | 1/2007 | Luo | |
| 2008/0027305 | A1 | 1/2008 | Gundel | |
| 2009/0262995 | A1 | 10/2009 | Futami et al. | |
| 2011/0249299 | A1* | 10/2011 | Wu | G06K 9/2063 |
| | | | | 358/3.26 |
| 2012/0020563 | A1* | 1/2012 | Amir | G06K 9/3266 |
| | | | | 382/182 |
| 2012/0106817 | A1* | 5/2012 | Shih | G06F 19/321 |
| | | | | 382/131 |
| 2013/0163860 | A1* | 6/2013 | Suzuki | G06K 9/00718 |
| | | | | 382/159 |
| 2014/0089000 | A1* | 3/2014 | Takata | G06F 19/321 |
| | | | | 705/2 |

OTHER PUBLICATIONS

Antani et al., "Exploring use of Images in Clinical Articles for Decision Support in Evidence-Based Medicine," Proc. SPIE 6815, Document Recognition and Retrieval XV, 68150Q, Jan. 28, 2008.*
You et al., "Figure content analysis for improved biomedical article retrieval," Electronic Imaging, SPIE vol. 7247, 72470V, 2009 (Year: 2009).*
Antani et al., "Exploring use of Images in Clinical Articles for Decision Support in Evidence-Based Medicine," Proc. SPIE 6815, Document Recognition and Retrieval XV, 68150Q, Jan. 28, 2008 (Year: 2008).*
You, D., "Figure content analysis for improved biomedical article retrieval", Proceedings of SPIE, vol. 7247, 2009.

* cited by examiner

... with a short axis distance of cm and a long axis distance of cm ...

FIG. 5

... with a short axis distance of 1.07 cm and a long axis distance of 3.35 cm ...

FIG. 6

... with a short axis distance of and a long axis distance of ...

FIG. 7

... with a short axis distance of 1.07 cm and a long axis distance of 3.35 cm ...

FIG. 8

... with a short axis of and a long axis of ...

FIG. 9

... with a short axis distance of 1.07 cm and a long axis distance of 3.35 cm ...

FIG. 10

EXTRACTION OF INFORMATION FROM AN IMAGE AND INCLUSION THEREOF IN A CLINICAL REPORT

CROSS-REFERENCE TO PRIOR APPLICATIONS

This application is the U.S. National Phase application under 35 U.S.C. § 371 of International Application No. PCT/IB2015/050214, filed on Jan. 12, 2015, which claims the benefit of U.S. Provisional Application No. 61/931,735, filed on Jan. 27, 2014. These applications are hereby incorporated by reference herein.

The following generally relates to extracting information from an image and including the extracted information in a clinical report corresponding to the image. Examples of suitable images are images generated by an imaging system such as an ultrasound (US) imaging system, a computed tomography (CT) imaging system, an X-ray, a magnetic resonance (MR) imaging system, a positron emission tomography (PET) imaging system, a single photon emission computer tomography (SPECT) imaging system and/or other imaging system.

FIG. 1 shows an example image 102. The image 102, generally, includes two separate regions 104 and 106. The region 104 is a medical image display region, and the region 106 is an information display region. In the illustrated example, the medical image display region is displaying an ultrasound image 108 with annotations (graphical in FIG. 1, but could also include textual) in overlays superimposed over the image. The annotations include marker pairs 110/112 and 114/116, which identify end points for distance measurements there between. In FIG. 1, the distances are in connection with a short and a long axis of a lesion represented in the image.

The information display region 106 displays alphanumeric information about the image, the imaging procedure, the imaging facility, the imaging apparatus, the patient, parameters measured in the image, etc. For example, in the illustrated embodiment, the information includes pixel intensity window and level settings 118, a type of procedure 120 and 122, a hospital name 124, a frequency of the ultrasound imaging frame rate 126, the side of the patient scanned 128, and distance measurements 130 and 132 (based on the marker pairs 110/112 and 114/116), along with the measurement type 134 and 136 and units 138 and 140. Other images include less or more information, information located in different regions, etc.

A reading clinician may want to include some or all annotations and/or alphanumeric information in a clinical report, which is in the form of an electronic formatted file, corresponding to the image. In instances in which the annotations and/or alphanumeric information are not readily accessible (e.g., not included in a DICOM header, not included in a dictation tape/file, not in a readable format by the viewing/reporting system, etc.), the person generating or updating the clinical report with the annotations and/or alphanumeric information has to manually enter the annotations and/or alphanumeric information, where possible.

However, manual entry of the annotations and/or alphanumeric information requires the user to look at the image 102, remember and/or write down the annotations and/or alphanumeric information of interest, look at the reporting generating running software application, and then add the annotations and/or alphanumeric information to the report. Unfortunately, this process can be tedious and consumes time, which could otherwise be spent with a patient and/or reading other images, for example, in the case where the reading physician or other medical staff adds the textual annotations and/or alphanumeric information to the clinical report.

Aspects described herein address the above-referenced problems and others.

The following describes an approach in which a viewing/reporting system extracts information from an image and incorporates the extracted information into a corresponding report.

In one aspect, a method includes obtaining, in electronic format, an image including a medical image display region and an information display region. The at least one of the medical image display region or the information display region includes graphical indicia representing at least one of an annotation or alphanumeric information. The method further includes evaluating pixels of the image to identify pixels including the graphical indicia representing an annotation or alphanumeric information of interest in the image. The method further includes extracting the annotation or alphanumeric information of interest from the identified graphical indicia from the image. The method further includes inserting the extracted annotation or alphanumeric information of interest in an electronically formatted clinical report for the image.

In another aspect, a computing system includes a computer readable storage medium with instructions including an information extraction module and a report generating/editing module. The computing system further includes a processor that executes the instructions. The processor, in response to executing the instructions, obtains, in electronic format, an image including a medical image display region and an information display region. The at least one of the medical image display region or the information display region includes graphical indicia representing at least one of an annotation or alphanumeric information. The processor, in response to executing the instructions, further evaluates pixels of the image to identify pixels including the graphical indicia representing an annotation or alphanumeric information of interest in the image. The processor, in response to executing the instructions, further extracts the annotation or alphanumeric information of interest from the identified graphical indicia from the image. The processor, in response to executing the instructions, further inserts the extracted annotation or alphanumeric information of interest in an electronic clinical report for the image.

In another aspect, a computer readable storage medium is encoded with computer readable instructions. The computer readable instructions, when executed by a processor, cause the processor to: obtain, in electronic format, an image including a medical image display region and an information display region. The at least one of the medical image display region or the information display region includes graphical indicia representing at least one of an annotation or alphanumeric information. The computer readable instructions, when executed by the processor, further cause the processor to: evaluate pixels of the image to identify pixels including the graphical indicia representing an annotation or alphanumeric information of interest in the image. The computer readable instructions, when executed by the processor, further cause the processor to: extract the annotation or alphanumeric information of interest from the identified graphical indicia from the image. The computer readable instructions, when executed by the processer, further cause the processor to: insert the extracted annotation or alphanumeric information of interest in an electronic clinical report for the image.

The invention may take form in various components and arrangements of components, and in various steps and arrangements of steps. The drawings are only for purposes of illustrating the preferred embodiments and are not to be construed as limiting the invention.

FIG. 1 illustrates an image with annotations and/or alphanumeric information.

FIG. 2 schematically illustrates an example viewing/reporting computing apparatus in connection with a plurality of imaging systems and a data repository.

FIG. 5 schematically illustrates a clinical report that does not include certain numerical values.

Figure 1:
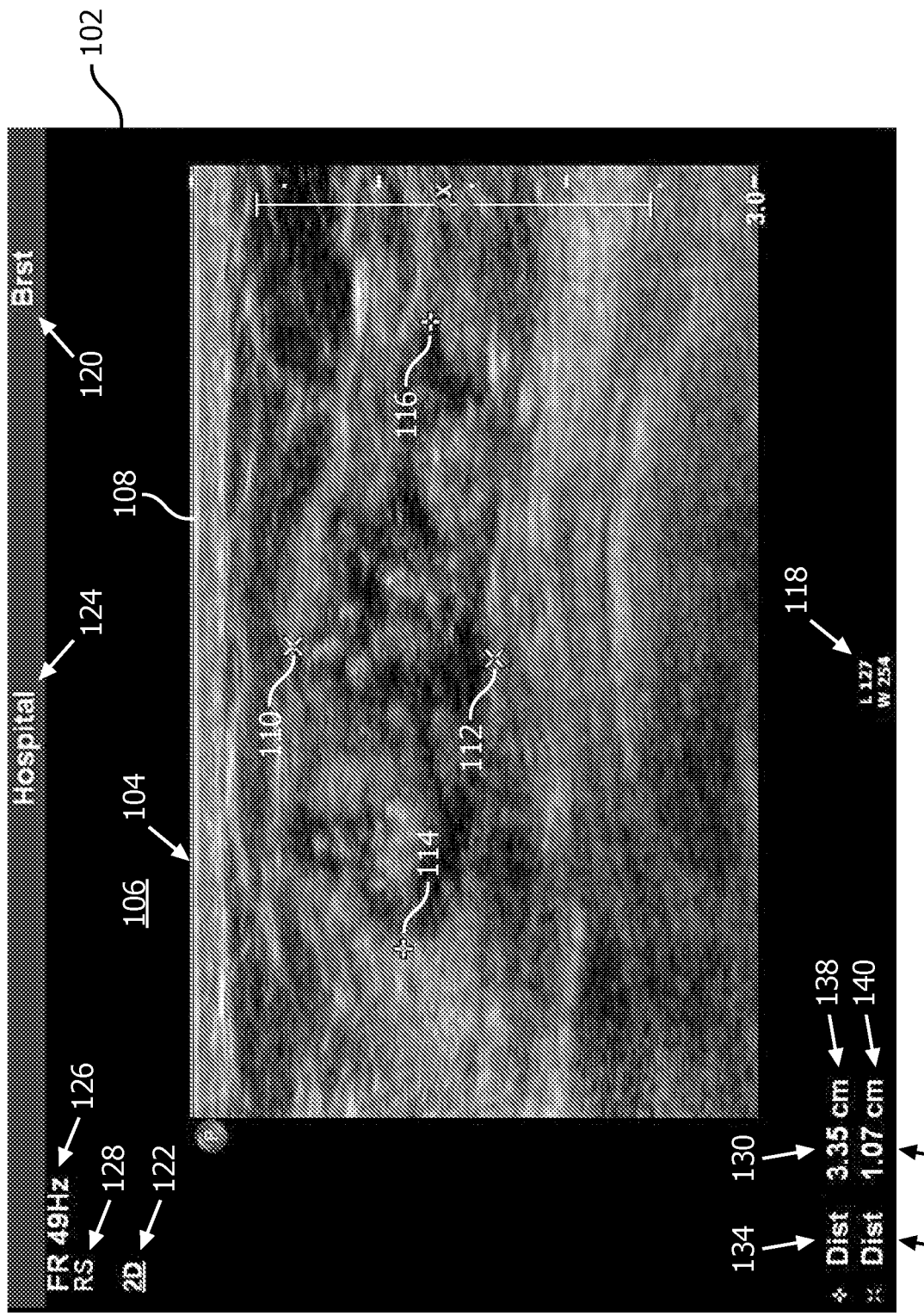

FIG. 6 schematically illustrates the clinical report of FIG. 5 after the extraction of the certain numerical values from the image of FIG. 1 and the inclusion thereof into the report.

FIG. 7 schematically illustrates a clinical report that does not include certain numerical values or the measurement units thereof.

FIG. 8 schematically illustrates the clinical report of FIG. 7 after the extraction of the certain numerical values and the measurement units thereof from the image of FIG. 1 and the inclusion thereof into the report.

FIG. 9 schematically illustrates a clinical report that does not include certain numerical values, the measurement units thereof or the type of the measurements.

FIG. 10 schematically illustrates the clinical report of FIG. 9 after the extraction of the certain numerical values, the measurement units thereof and the type of the measurements from the image of FIG. 1 and the inclusion thereof into the report.

Figure 2:
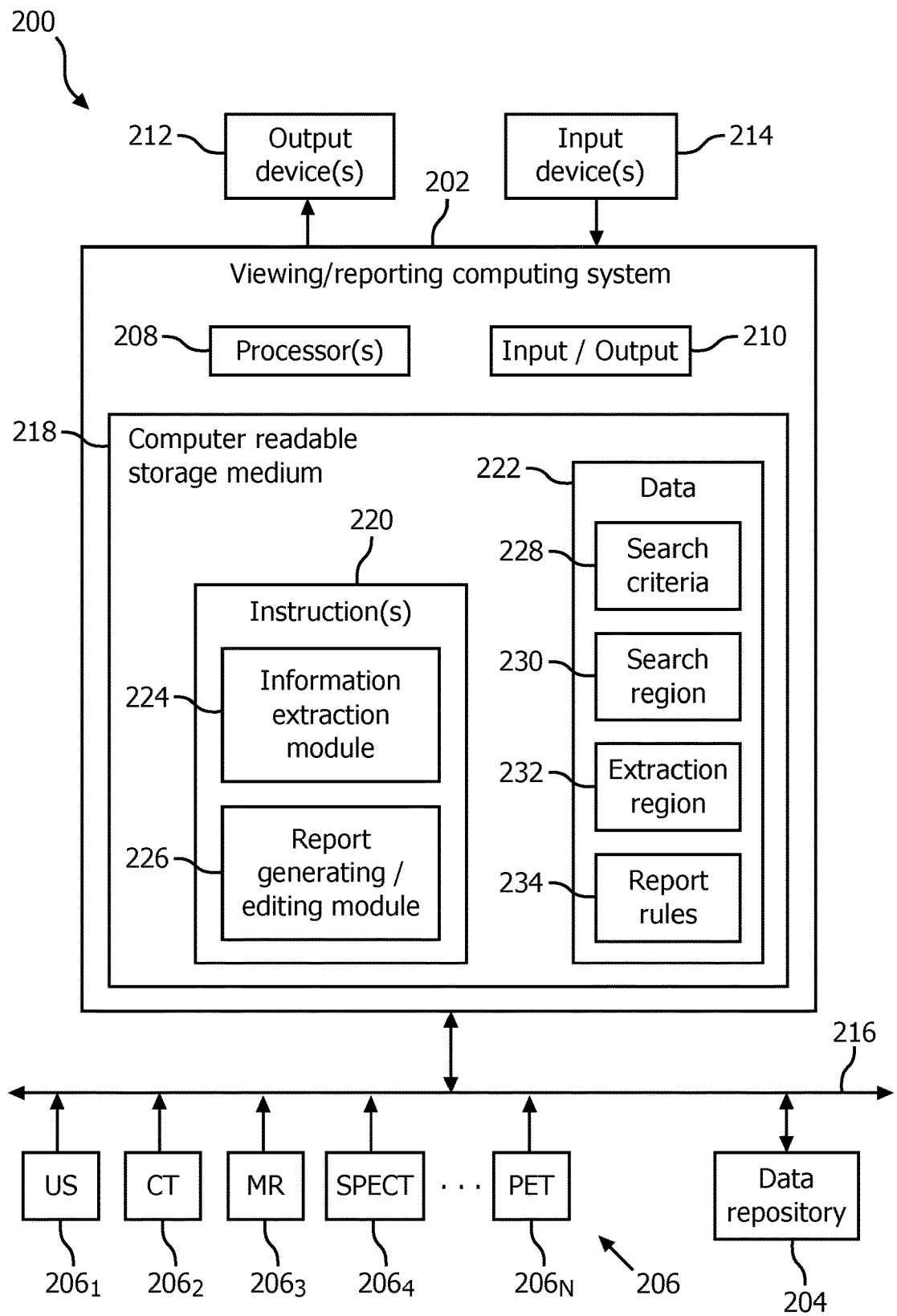

Initially referring to FIG. 2, a system 200 is schematically illustrated. The system 200 that includes a viewing/reporting computing apparatus 202 in connection with a data repository 204 and N imaging systems 206, where N is an integer equal to or greater than one. In the illustrated embodiment, the viewing/reporting computing apparatus 202 receives images in electronic format from the imaging systems 206 and/or the data repository 204. The images include pixels with gray scale and/or color intensity values and annotations and/or alphanumeric information either burned into the image or overlaid there over.

The N imaging systems 206 include one or more of an ultrasound (US) scanner $206_1$, a computed tomography (CT) scanner $206_2$, a magnetic resonance (MR) scanner $206_3$, a single photon emission computer tomography (SPECT) scanner $206_1$, . . . , and a positron emission tomography (PET) scanner $206_N$. The data repository 204 includes one or more of a picture archiving and communication system (PACS), a radiology information system (RIS), a hospital information system (HIS), an electronic medical record (EMR), a database, a server, an imaging system, and/or other data repository.

The viewing/reporting computing apparatus 202 is, for example, a computer such as a desktop, a laptop, and/or other computer. As such, the viewing/reporting computing apparatus 202 includes a processor 208 (e.g., a central processing unit or CPU, a microprocessor, or the like). The viewing/reporting computing apparatus 202 further includes input/output (I/O) 210 that facilitates communication with at least an output device(s) 212 such as a display monitor, a filmer, etc., an input device(s) 214 such as a mouse, keyboard, a touch sensitive region of a touchscreen, etc., and a network 216.

The viewing/reporting computing apparatus 202 further includes a computer readable storage medium 218, which excludes transitory medium, such as physical memory and/or other non-transitory memory. The computer readable storage medium 218 stores computer readable instructions 220 and data 222. The processor 208 executes the computer readable instructions 220 stored in the computer readable storage medium 218. The processor 208 can also execute computer readable instructions carried by a signal, carrier wave, and other transitory (i.e., non-computer readable storage) medium.

In the illustrated example, the instructions 218 include at least an information extraction module 224 and a report generating/editing module 226. The data 222 includes at least search criteria 228, a search region 230, an extraction region 232, and report (inclusion) rules 234. As described in greater detail below, the information extraction module 224 locates indicia including at least annotations and/or alphanumeric information of interest from a received image based on the search criteria 228 and the search region 230 and extracts the at least annotations and/or alphanumeric information of interest based on the extraction region 232, and the report generating/editing module 226 inserts the extracted annotations and/or alphanumeric information in a clinical report for the image based on the report rules 234.

Figure 3:
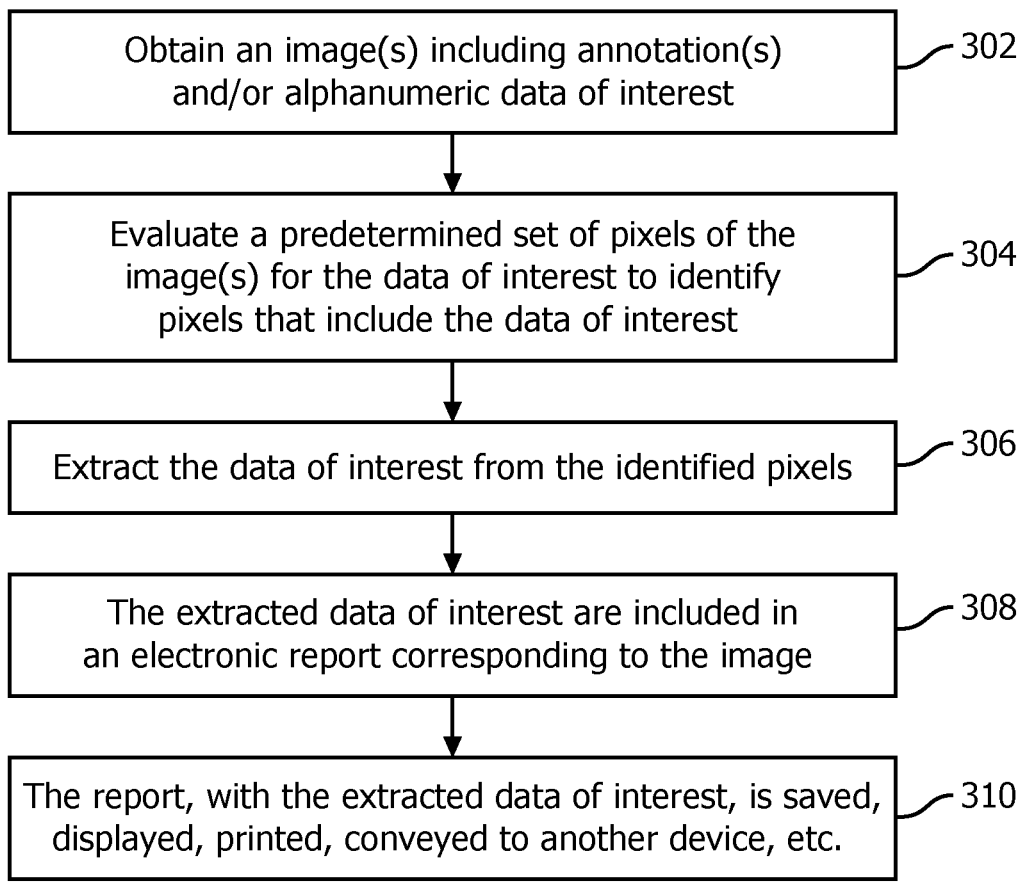
FIG. 3 illustrates an example method for extracting annotations and/or alphanumeric information from an image and including the extracted annotations and/or alphanumeric information in a clinical report corresponding to the image.

FIG. 3 illustrates an example method extracting annotations and/or alphanumeric information from an image and including the extracted annotations and/or alphanumeric information in a clinical report corresponding to the image.

It is to be appreciated that the ordering of the acts in the methods is not limiting. As such, other orderings are contemplated herein. In addition, one or more acts may be omitted and/or one or more additional acts may be included.

At 302, an image(s), which includes annotations and/or alphanumeric information of interest, is obtained.

As discussed herein, the image is received at the viewing/reporting computing system 202 as a file(s) in electronic format, and the annotations and/or alphanumeric information are part of the image and not separate data.

At 304, sets of pixels of the image are evaluated to identify pixels that include the annotations and/or alphanumeric information of interest based on the search criteria 228 and the search region 230. The pixels are identified, for example, using a template mapping approach such as character recognition, a compositional model, learning based classifiers, and/or other approach.

The search criteria 228 identifies the indicia to search and the number and group of the pixels in each set. For example, where character recognition is being used, the search criteria 228 is an alphanumeric character and set of pixels may be individual pixels, a string (e.g., 10, etc. successive) of pixels, or a two dimensional block (e.g., a 5×5, a 10×2, etc.) of pixels. The indicia to search is, for example, a predetermined default and/or user defined. For the latter, a user, for example, defines the indicia before the search and/or provides the indicia at the time of the search. The set of pixels, in one instance, is generic to the image. However, in a variation, the set of pixels takes into account image resolution.

The search region 230 identifies the sub-regions within the image to search. In one instance, the identified sub-regions cover the entire image. In another instance, the identified sub-regions cover less than the entire image, for example, only the region where the annotations and/or alphanumeric information are displayed. In one example, the sub-region is the sub-portion of the image that is only outside of the region where the medical image is displayed. In yet another example, the sub-region is only the displayed medical image of the image.

At 306, the annotations and/or alphanumeric information data of interest is extracted from the identified pixels based on the extraction region 232.

For example, the extraction region 232 may indicate that only the pixels including the indicia are extracted. This is well-suited for situations where the search criteria includes the annotations and/or alphanumeric information data of interest. In another example, the extraction region 232 may indicate that only a predetermined number of pixels preceding the pixels including the indicia are extracted. This is well-suited for situations where the search criteria includes indicia that follows the annotations and/or alphanumeric information data of interest.

In yet another example, the extraction region 232 may indicate that only a predetermined number of pixels succeeding the pixels including the indicia are extracted. This is well-suited for situations where the search criteria includes indicia that precedes the annotations and/or alphanumeric information data of interest. In still another example, the extraction region 232 may indicate that pixels that precede, succeed, and/or only include the pixels including the indicia are extracted. The number of preceding and succeeding pixels can be the same or different. Other approaches are also contemplated herein.

At 308, the extracted annotations and/or alphanumeric information is included in an electronically formatted clinical report corresponding to the image.

As discussed herein, the annotations and/or alphanumeric information are included based on the report rules 234. In one instance, the report rules 234 identify a predetermined location in the report. In another instance, the report rules 234 insert the annotations and/or alphanumeric information at a user identified location. The report rules 234, in one instance, indicate that only a numeric sub-portion or an alphabetic sub-portion of the annotations and/or alphanumeric information is included in report.

At 310, the clinical report with the included extracted annotations and/or alphanumeric information is saved to computer readable storage medium, displayed via a display monitor, printed to paper, conveyed (in electronic format) to another device, etc.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

Figure 4:
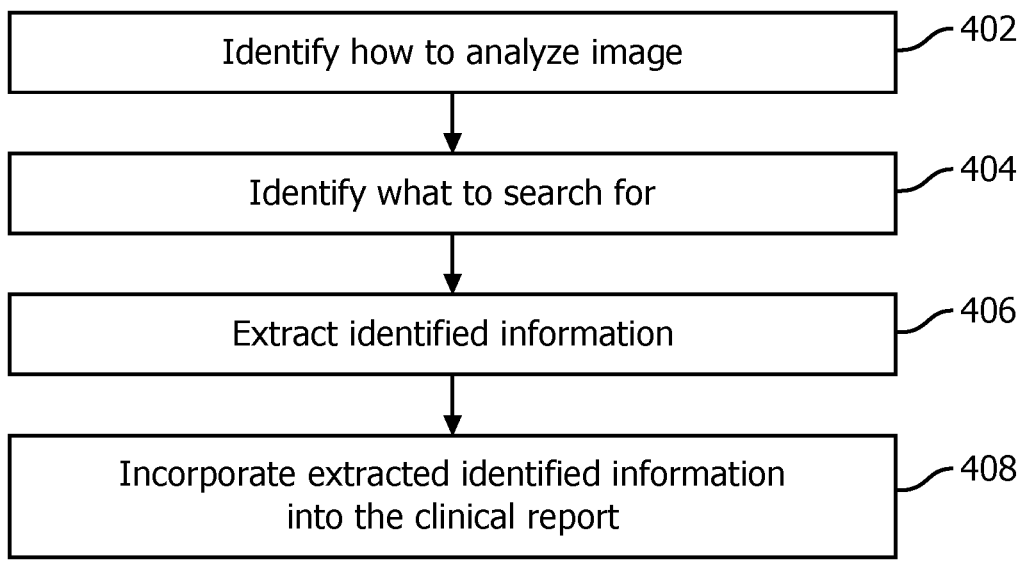
FIG. 4 illustrates an example method for extracting numerical measurement values of lesion short and long axes from indicia of an image and including the extracted numerical measurement values in a clinical report corresponding to the image.

A specific example is described next in connection with FIGS. 1 and 4-10. As with FIG. 3, the ordering of the acts of FIG. 4 is not limiting such that other orderings are contemplated herein. In addition, one or more acts may be omitted and/or one or more additional acts may be included.

In this example, the short and long axes of the lesion represented via pixels of an ultrasound image 108 displayed in the display region 104 of FIG. 1 are measured based on the maker pairs 110/112 and 114/116 and indicia representing the measurements is placed on the image and subsequently extracted and included in a clinical report. Lesions, in general, may be related to diseases such as cancer. The size of a lesion impacts the diagnosis; a large size is often related to the malignancy of the lesion. Accurate measurement of lesion size is used for clinical diagnosis, progress of a disease, and therapy management decisions.

With reference to FIG. 4, at 402, the search criteria 228 (FIG. 2) indicates how the image is analyzed. For instance, in one instance, the entire image is analyzed pixel-by-pixel until the graphical indicia of interest is located via character recognition and/or otherwise. In a variation, groups of two or more pixels are analyzed until the indicia of interest is located. In a variation, only the region 106 outside of the image display region 104 is analyzed. In still another variation, only a sub-section (e.g., lower left quadrant) of the image 102 is analyzed.

In yet another instance, for example, where the indicia of interest are superimposed over the image 108, only the image display region 104 is analyzed. At 404, the search criteria 228 (FIG. 2) indicates the information to be extracted by the information extraction module 224 (FIG. 2). In the illustrated example, the search criteria 228 includes alphabetic characters representing the units of the numerical value of interest. In this instance, the search criteria is "mm," "cm," and/or other units, using an abbreviation (as shown) or the entire word.

Additionally or alternatively, the search criteria 228 includes alphabetic characters that represent the measurement type. Examples of this data include "dist," "area," "volume," "std," "var," and/or other measurement type, using an abbreviation (as shown in FIG. 1) or the entire word. In a variation, the search criteria 228 includes the characters that are used to visually identify the markers 110, 112, 114, and 116 overlaid over the image 108 and included along with the indicia representing the numerical values. In the illustrated example, the characters would be  and .

Once a group of pixels is identified based on the search criteria 228 and the search region 230, at 406, the numerical values are extracted from the image 102. Where the search criteria is "cm" at least a predetermined number of pixels that precede the search criteria is extracted. In the illustrated example, the predetermined number of pixels would ensure that the numerical values 130 and/or 132 are extracted. Where the search criteria is "Dist", at least a predetermined number of pixels that succeed the search criteria is extracted. In the illustrated example, the predetermined number of pixels would ensure that the numerical values 130 and/or 132 are extracted.

Where the search criteria is a numerical digit (e.g., 0, 1, 2, . . . , 9, etc.) at least a predetermined number of pixels that cover the search criteria is extracted. In the illustrated example, likewise the predetermined number of pixels would ensure that the numerical values 130 and/or 132 are extracted. In all three of these examples, additional pixels, preceding and/or succeeding the predetermined number of pixels, can further be extracted. Other approaches, including a combination of the above three approaches, are also contemplated herein.

At 408, the extracted numerical values are incorporated in an electronically formatted clinical report for the image based on the report rules 232. Several examples are shown in connection with FIGS. 5, 6, 7, 8, 9, and 10. The location in the electronically formatted report can be predetermined (as shown) and/or based on a user selected location. With a predetermined location, character recognition can be used to locate words to the left and right of the desired location.

FIGS. 5 and 6 show a sub-portion of a report where only the numeric values are inserted in the report. FIGS. 7 and 8 show a sub-portion of a report where the numeric values and the units of measurement are inserted in the report. FIGS. 9 and 10 show a sub-portion of a report where the numeric values, the units of measurement and the measurement type are inserted in the report. FIGS. 5, 7 and 9 represent the report prior to inclusion of the alphanumeric data of interest, and FIGS. 6, 8 and 10 represent the report after the inclusion of the alphanumeric data of interest.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
obtaining, in electronic format, an image including a medical image display region and an information display region, wherein at least one of the medical image display region or the information display region includes an alphanumeric graphical indicia representing an alphanumeric information, and the medical image display region includes an annotation graphical indicia representing a non-textual annotation within the medical image display region;
evaluating pixels of the image to identify a first group of pixels including the alphanumeric graphical indicia representing the alphanumeric information of interest in the image and to identify a second group of pixels including the annotation graphical indicia representing the non-textual annotation of interest in the image;
determining first and second extraction groups of pixels based on first and second predetermined extraction regions, wherein the first extraction group of pixels includes the pixels identified as including the alphanumeric graphical indicia and at least one of: a predetermined number of pixels preceding the pixels identified as including the alphanumeric graphical indicia and a predetermined number of pixels succeeding the pixels identified as including the alphanumeric graphical indicia, and wherein the second extraction group of pixels includes the pixels identified as including the annotation graphical indicia and at least one of: a predetermined number of pixels preceding the pixels identified as including the annotation graphical indicia and a predetermined number of pixels succeeding the pixels identified as including the annotation graphical indicia;
extracting the first extraction group of pixels to extract the alphanumeric information, and extracting, without modifying the medical image display region, the second extraction group of pixels to extract the non-textual annotation; and
inserting the extracted alphanumeric information and extracted non-textual annotation in an electronically formatted clinical report corresponding to the image, wherein inserting the extracted alphanumeric information and extracted non-textual annotation comprises inserting the alphanumeric information into a first predetermined location within the electronically formatted clinical report corresponding to the image, and inserting the extracted non-textual annotation into a second predetermined location within the electronically formatted clinical report corresponding to the image, the first and second predetermined locations corresponding to the image and defined by a set of predetermined report rules.

2. The method of claim 1, further comprising:
determining a group of search pixels based on a predetermined search region; and
evaluating the group of search pixels to identify the pixels including the graphical indicia.

3. The method of claim 1, further comprising:
searching the entire image for the graphical indicia.

4. The method of claim 1, further comprising:
determining a search region of the image to search, wherein the search region is a sub-region of the image; and
searching only the search region of the image for the graphical indicia.

5. The method of claim 4, wherein the sub-region includes one of only the medical image display region or only the information display region.

6. The method of claim 1, further comprising:
employing character recognition to identify the pixels including the graphical indicia.

7. The method of claim 1, wherein the identified pixels of the non-textual annotation graphical indicia represent at least one of a numerical distance measurement between at least two user-identified locations in the image, a measurement unit of the measurement, or a measurement type of the measurement.

8. The method of claim 1, wherein the predetermined location corresponds to a user-identified location.

9. The method of claim 1, wherein the extraction group of pixels includes only the pixels identified as including indicia.

10. A computing system, comprising:
a non-transitory computer readable storage medium with instructions including an information extraction module and a report generating/editing module; and a processor, which, in response to executing the instructions:
obtains, in electronic format, an image including a medical image display region and an information display region, wherein at least one of the medical image display region and the information display region includes an alphanumeric graphical indicia representing an alphanumeric information, and the medical image display region includes an annotation graphical indicia representing a non-textual annotation within the medical image display region
evaluates pixels of the image to identify a first group of pixels including the alphanumeric graphical indicia, and to identify a second group of pixels including the annotation graphical indicia representing the non-textual annotation of interest in the image;
determines first and second extraction groups of pixels based on first and second predetermined extraction regions, wherein the first extraction group of pixels includes the pixels identified as including the alphanumeric graphical indicia and at least one of: a predetermined number of pixels preceding the pixels identified as including the alphanumeric graphical indicia or succeeding the pixels identified as including the alphanumeric graphical indicia, and wherein the second extraction group of pixels includes the pixels identified as including the annotation graphical indicia and at least one of: a predetermined number of pixels preceding the pixels identified as including the annotation graphical indicia and a predetermined number of pixels succeeding the pixels identified as including the annotation graphical indicia; and
extracts the first extraction group of pixels to extract the alphanumeric information, and extracts, without modifying the medical image display region, the second extraction group of pixels to extract the non-textual annotation; and inserts the extracted alphanumeric information and extracted non-textual annotation in an electronically formatted clinical report corresponding to the image, wherein inserting the extracted alphanumeric information and extracted non-textual annotation comprises inserting the alphanumeric information into a first predetermined location within the electronic clinical report corresponding to the image, and inserts the extracted non-textual annotation into a second predetermined location within the electronically formatted clinical report corresponding to the image, the first and second predetermined locations defined by a set of predetermined report rules.

11. A non-transitory computer readable storage medium encoded with computer readable instructions, which, when executed by a processor, cause the processor to:

obtain, in electronic format, an image including a medical image display region and an information display region, wherein at least one of the medical image display region and the information display region includes an alphanumeric graphical indicia representing alphanumeric information, and the medical image display region includes an annotation graphical indicia representing a non-textual annotation within the medical image display region;

evaluate pixels of the image to identify a first group of pixels including the alphanumeric graphical indicia representing the alphanumeric information of interest in the image and to identify a second group of pixels including the annotation graphical indicia representing the non-textual annotation of interest in the image;

determine first and second extraction groups of pixels based on first and second predetermined extraction regions, wherein the first extraction group of pixels includes the pixels identified as including the alphanumeric graphical indicia and at least one of: a predetermined number of pixels preceding the pixels identified as including the alphanumeric graphical indicia and a predetermined number of pixels succeeding the pixels identified as including the alphanumeric graphical indicia, and wherein the second extraction group of pixels includes the pixels identified as including the annotation graphical indicia and at least one of: a predetermined number of pixels preceding the pixels identified as including the annotation graphical indicia and a predetermined number of pixels succeeding the pixels identified as including the annotation graphical indicia;

extract the first extraction group of pixels to extract the alphanumeric information in response to identifying the graphical indicia, and extract, without modifying the medical image display region, the second extraction group of pixels to extract the non-textual annotation; and insert the extracted alphanumeric information and extracted non-textual annotation in an electronic clinical report corresponding to the image, wherein inserting the extracted alphanumeric information and extracted non-textual annotation comprises inserting the alphanumeric information into a predetermined location within the electronic clinical report corresponding to the image, and comprises inserting the extracted non-textual annotation into a second predetermined location within the electronically formatted clinical report corresponding to the image, the first and second predetermined locations defined by a set of predetermined report rules.

* * * * *